(12) United States Patent
Gupta et al.

(10) Patent No.: US 8,633,124 B2
(45) Date of Patent: Jan. 21, 2014

(54) SPHEROIDAL PARTICLES FOR OLEFIN POLYMERIZATION CATALYST

(75) Inventors: Virendrakumar Gupta, Mumbai (IN); Saurabh Singh, Mumbai (IN); Umesh Makwana, Mumbai (IN); Jomichan Joseph, Mumbai (IN); Kamlesh Singala, Mumbai (IN); Smitha Rajesh, Mumbai (IN); Vallabhbhai Patel, Mumbai (IN); Mukeshkumar Yadav, Mumbai (IN); Gurmeet Singh, Mumbai (IN)

(73) Assignee: Reliance Industries Limited, Mumbai (IN)

( * ) Notice: Subject to any disclaimer, the term of this patent is extended or adjusted under 35 U.S.C. 154(b) by 407 days.

(21) Appl. No.: 12/989,230

(22) PCT Filed: Sep. 1, 2008

(86) PCT No.: PCT/IN2008/000555
§ 371 (c)(1),
(2), (4) Date: Oct. 22, 2010

(87) PCT Pub. No.: WO2009/130707
PCT Pub. Date: Oct. 29, 2009

(65) Prior Publication Data
US 2011/0054129 A1 Mar. 3, 2011

(30) Foreign Application Priority Data
Apr. 25, 2008 (IN) .............. 916/MUM/2008

(51) Int. Cl.
*C08F 4/02* (2006.01)
*B01J 31/00* (2006.01)

(52) U.S. Cl.
USPC ............ 502/111; 502/112; 502/115; 502/156

(58) Field of Classification Search
USPC .......................... 502/112, 115, 156
See application file for complete search history.

(56) References Cited

U.S. PATENT DOCUMENTS

| 7,737,069 B2 * | 6/2010 | Tanase et al. ............... 502/102 |
| 2001/0012908 A1 | 8/2001 | Tanase et al. |

FOREIGN PATENT DOCUMENTS

| EP | 1508559 | 2/2005 |
| EP | 1783109 | 5/2007 |

(Continued)

OTHER PUBLICATIONS

International Search Report dated Dec. 1, 2009 for related International Application No. PCT/IN2008/000555.

*Primary Examiner* — David W Wu
*Assistant Examiner* — Elizabeth Eng
(74) *Attorney, Agent, or Firm* — Klein, O'Neill & Singh, LLP

(57) ABSTRACT

The invention relates to a process for the synthesis of spheroidal magnesium alkoxide having improved mechanical strength and narrow particle size distribution, the process comprising reacting magnesium metal, in the presence of iodine, with a mixture of alcohols by step-wise heating first in the range of 40° C. to 65° C. for a period of 2 hours and then in the range of 65° C. to 80° C. for a period of 1 hour, further by maintaining reaction temperature at 80° C. for a period of 6-10 hours, the vapors of the mixture produced during the reaction being condensed in an overhead condenser, hydrogen gas produced during the reaction being vented off and the mixture of alcohols left after the reaction being filtered and reused. The invention also relates to spheroidal magnesium alkoxide particles synthesized by the method, to the Ziegler natta procatalyst synthesized by using the alkoxide and to the polymer resin synthesized using the procatalyst.

7 Claims, 3 Drawing Sheets

(56) References Cited

FOREIGN PATENT DOCUMENTS

Figure 1:
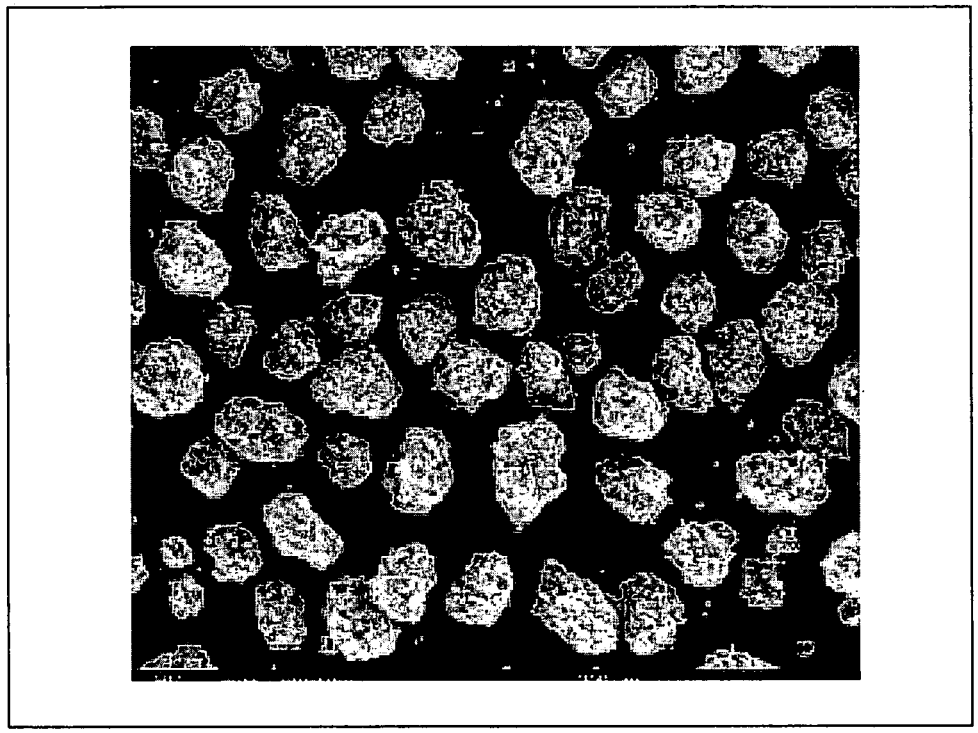

| EP | 2006272 | 12/2008 |
| WO | WO2005/044873 | 5/2005 |
| WO | WO 2005102973 A1 * 11/2005 | ............ C07C 31/28 |
| WO | WO2006/033512 | 3/2006 |

* cited by examiner

SPHEROIDAL PARTICLES FOR OLEFIN POLYMERIZATION CATALYST

FIELD OF INVENTION

The invention relates to spheroidal magnesium alkoxide particles having improved mechanical strength and narrow particle size distribution. The invention also relates to a method for synthesis of the alkoxide, to the Ziegler Natta procatalyst synthesized by using the alkoxide and to the polymer resin synthesised using the procatalyst.

BACKGROUND OF INVENTION

Resin particles having regular shape and narrow particle size distribution are desirable for good flowability during resin extrusion. They are also essential to produce regular shaped copolymer products with uniform rubber dispersion. Shape regularity and size distribution of polymer resin are usually related to the shape and size of the catalyst particles as well as of the solid reactants from which the catalyst particles are synthesized. Solid magnesium ethoxide is used as the reactant for the synthesis of Ziegler Natta catalysts used for olefin polymerization.

WO 2005/044873 discloses a method for synthesizing spherical magnesium alkoxide particles by reacting magnesium with an alcohol mixture at a temperature below the boiling point of the mixture. The spherical magnesium alkoxide particles synthesized by the method are rather frangible and do not retain their morphology or particle size during the synthesis of Ziegler Natta procatalyst, especially when the procatalyst synthesis is carried out on a large scale. Further, the particle size distribution of the alkoxide particles synthesized by the above mentioned method need improvement.

DETAILED DESCRIPTION

Accordingly, the invention provides a process for synthesis of spheroidal magnesium alkoxide particles having improved mechanical strength and narrow particle size distribution.

In one embodiment, the invention provides a process for the synthesis of spheroidal magnesium alkoxide having improved mechanical strength and narrow particle size distribution, the process comprising reacting magnesium metal, in the presence of iodine, with a mixture of alcohols by step-wise heating first in the range of 40° C. to 65° C. for a period of 2 hours and then in the range of 65° C. to 80° C. for a period of 1 hour, further by maintaining reaction temperature at 80° C. for a period of 6 to 10 hours, the vapours of the mixture produced during the reaction being condensed in an overhead condenser, hydrogen gas produced during the reaction being vented off and the mixture of alcohols left after the reaction being filtered and reused.

In another embodiment, the invention provides a process for the synthesis of spheroidal magnesium alkoxide having improved mechanical strength and narrow particle size distribution, the process comprising reacting magnesium metal, in the presence of iodine, with a mixture of alcohols by step-wise heating first in the range of 40° C. to 65° C. for a period of 2 hours and then in the range of 65° C. to 80° C. for a period of 1 hour, further by maintaining reaction temperature at 80° C. for a period of 6 to 10 hours, the vapours of the mixture produced during the reaction being condensed in an overhead condenser, hydrogen gas produced during the reaction being vented off and the mixture of alcohols left after the reaction being filtered and reused, the mixture of alcohols being selected from the group consisting of methanol, ethanol, propanol, isopropanol, butanol and isobutanol.

In another embodiment, the invention provides a process for the synthesis of spheroidal magnesium alkoxide having improved mechanical strength and narrow particle size distribution, the process comprising reacting magnesium metal, in the presence of iodine, with a mixture of alcohols by step-wise heating first in the range of 40° C. to 65° C. for a period of 2 hours and then in the range of 65° C. to 80° C. for a period of 1 hour, further by maintaining reaction temperature at 80° C. for a period of 6 to 10 hours, the vapours of the mixture produced during the reaction being condensed in an overhead condenser, hydrogen gas produced during the reaction being vented off and the mixture of alcohols left after the reaction being filtered and reused, ratio of magnesium metal to the mixture of alcohols being in the range of 1:2 to 1:20

In another embodiment, the invention provides spheroidal magnesium alkoxide particles, the particles comprising at least two different alkoxy groups, one alkoxy group being present in less than 40 percentage by weight and another alkoxy group being present in greater than 40 percentage by weight of the particles.

In another embodiment, the invention provides spheroidal magnesium alkoxide particles having circularity in the range of 0.5 to 1.0, mean particle size in the range of 25 to 65 microns, bulk density in the range of 0.45 to 0.65 g/cc, span less than 1.5, surface area in the range of 1 to 20 $m^2/g$ and crushing strength of at least 20 kg.

In another embodiment, the invention provides spheroidal magnesium alkoxide particles exhibiting a diffraction pattern on irradiation with a Cu Ka radiation having a wavelength of 1.5406 A°, the diffraction pattern comprising peaks at 2 θ values of around 9.8, 10.2, 10.4 and 11.9.

In another embodiment, the invention provides a method for synthesis of Ziegler Nata procatalyst, the method comprising reacting spheroidal magnesium alkoxide particles with $TiCl_4$ and chlorobenzene, the method yielding a side product having the formula $TiCl_x(OR^1)_y(OR^2)_z$, where x, y, z is an integer from 0 to 4 and $R^1$, $R^2$ is an alkyl or an aryl group, the side product on treatment with a carboxylic acid chloride generating in situ internal donors for the procatalyst.

In another embodiment, the invention provides spheroidal Ziegler Natta procatalyst having a particle size in the range of 25 to 65 microns and comprising internal donor(s) generated in situ In another embodiment, the invention provides spheroidal Ziegler Natta procatalyst comprising internal donor(s) selected from the group consisting of methyl benzoate, ethyl benzoate, n-propyl benzoate, i-propyl benzoate, n-butyl benzoate, i-butyl benzoate, dimethyl phthalate, diethyl phthalate, dipropyl phthalate, di-isopropyl phthalate, di-butyl phthalate and di-isobutyl phthalate In a further embodiment, the invention provides a method for polymerization of olefin, the method comprising contacting the olefin with a catalyst system comprising spheroidal Ziegler Natta procatalyst, triethyl alumunium cocatalyst optionally along with a selectivity control agent.

In a still further embodiment of the invention, there is provided spheroidal polyolefin particles synthesised by the method comprising contacting the olefin with a catalyst system comprising spheroidal Ziegler Natta procatalyst, triethyl alumunium cocatalyst optionally along with a selectivity control agent.

The invention provides a process for synthesis of spheroidal magnesium alkoxides having improved mechanical strength and narrow particle size distribution by reacting magnesium metal with a mixture of alcohols. The magnesium metal can be in the form of powder, granules or ribbon. The ratio of magnesium to the mixture of alcohols can be in the range of 1:2 to 1:20. The reaction is usually carried out at a temperature in the range of 20° C. to 100° C. and at a pressure of 0.1 to 5.0 atm. Reaction temperature is increased in a step wise manner to have improved kinetic control. The vapours of the alcohol mixture was recovered by condensing in the overhead condenser. The alcohol mixture left after the reaction was filtered and the filtrate was reused for the synthesis. The hydrogen gas produced during the synthesis was vented off. The reaction is carried out in the presence of an initiator such as iodine. Any halogen or halogen containing compound other than iodine can as well be used as the initiator. The mixture of alcohols used for the reaction is selected from the group consisting of methanol, ethanol, propanol, isopropanol, butanol and isobutanol. Other aliphatic/aromatic alcohols can as well be used for the reaction. Preferably, the mixture contain two alcohols, one of which is ethanol. One of the alcohols in the mixture is used in excess to work as the reaction solvent. Further, the reaction is carried out under inert atmosphere. The inert atmosphere is created in situ by hydrogen gas which is produced during the reaction.

The spheroidal magnesium alkoxide particles of the invention comprise at least two different alkoxy groups, one alkoxy group being present in less than 40 percentage by weight and another alkoxy group being present in greater than 40 percentage by total weight of the particles. Preferably the alkoxy group that is present in greater than 40 percentage by weight of the total alkoxy content is an ethoxy group. The alkoxide particles of the invention have low surface area, typically in the range of 1 to 20 m$^2$/g. Apart from its utility in the synthesis of spheroidal Ziegler Natta procatalyst, the spheroidal alkoxide particles of the invention can be used for other applications as well. The spheroidal alkoxide particles of the invention can be used for coating inorganic support materials such as silica or zeolites.

The spheroidal magnesium alkoxide particles of the invention are used for the synthesis of spheroidal Ziegler Natta procatalyst. The alkoxide particles can be optionally pretreated with titanium tetrachloride, before the procatalyst synthesis. The pretreatment is usually carried out by a 2-5 wt % solution of titanium tetrachloride in aromatic or aliphatic solvent. The procatalyst synthesis involves reaction of the magnesium alkoxide particles with TiCl$_4$ and chlorobenzene wherein TiCl$_x$(OR$^1$)$_y$(OR$^2$)$_z$, where x, y, z is an integer from 0 to 4 and R$^1$, R$^2$ is an alkyl or aryl group, is formed as a side product along with the procatalyst, during the synthesis. The side product is treated with a carboxylic acid chloride and the treatment results in the generation of internal donors. The preferred carboxylic acid chloride is benzoyl chloride. The quantity of in situ generated internal donors and consequently the composition of the procatalyst can be varied by varying the composition of magnesium alkoxide and amount of carboxylic acid chloride used for the treatment. The internal donors are used up during the synthesis of the procatalyst. The spheroidal procatalyst can be a diester based catalyst or a monoester based catalyst. Depending upon the specific requirements, catalysts based on other kind of internal donors can be prepared. Further, the spheroidal alkoxide particles of the invention can be used for the synthesis of spheroidal procatalyst on a large scale. The spheroidal procatalyst of the invention is used for the synthesis of spheroidal/regular shaped polyolefin resin having narrow particle size distribution and improved particle size. The molecular weight distribution of the polyolefin can be varied by varying the composition of internal donor in the catalyst.

The invention provides an economical method for synthesis of spheroidal magnesium alkoxide particles by recovering and reusing the mixture of alcohols used for the synthesis. The mixture of solvents is recovered through the vent condenser during the drying of the cake obtained after the reaction. Filtrate collected during slurry filtration is also directly reused. Further, the invention provides spheroidal magnesium alkoxide particles having regular shape, with narrow particle size distribution, high bulk density, high mechanical strength and crystallinity.

The magnesium alkoxide particles, the Ziegler natta procatalyst and the polyolefin resin in the following examples have been characterised by various methods. The alkoxy content of the alkoxide particles are measured by gas chromatography of the solution made by hydrolyzing magnesium alkoxide in dilute mineral acid. The mean particle size and span is obtained by particle size analyzer using laser and optical diffraction method on CILAS 1180 particle size analyzer. Span is calculated by ratio of $(D_{90}-D_{10})/D_{50}$ where if $D_n$=X microns then it signifies that n % of the total particle population is below X microns. Bulk density is measured by measuring the tapped volume and weight of certain quantity of powder and by dividing weight of the powder by the tapped volume. The circularity is measured from the analysis of scanning electron microscope image using an image analysis software. Circularity of a particle is =(area of 2 dimensional particle image)/(area of circle having same parameter as the particle). X-ray powder patterns were recorded using Bruker Advance D8 diffractometer. Morphology was explored with FEI Inspect Scanning Electron Microscope. Crushing strength was determined by applying a force increasing with constant rate to fixed volume of solid powder mass in a cylindrical vessel and determining the minimum force required for compressing the mass by 1 mm on vertical axis of force application. Donor content is determined using high pressure liquid chromatography of the catalyst solution in methanol. Polymer bulk density is calculated by measuring tapped volume and weight of fixed polymer resin quantity and then dividing weight by volume.

The invention is further illustrated by way of the following examples

EXAMPLES

Example 1

Synthesis of Spheroidal Magnesium Alkoxide Particles with Stepwise Heating of Reactants Magnesium powder (5.5 kg) was added to mixture of ethanol and methanol (125 L) in presence of initiator iodine (150 gm) at 40° C. with continued stirring. Making use of reaction exothermicity and external temperature control, reaction was conducted in a step-wise manner, heating first in the range to 40° C. to 65° C. for a period of 2 hrs and then in the range of 65° C. to 80° C. for a period of 1 hour, further by maintaining reaction temperature at 80° C. for a period of 7 hours. The vapours of the mixture produced during the reaction was condensed in an overhead condenser. The hydrogen gas produced during the reaction was vented off and the mixture of alcohols left after the reaction was removed by filtration. The filtrate was reused for the synthesis. A wet cake was obtained after removal of the filtrate. The wet cake was dried to obtain 25 kg of white free flowing spheroidal particles having a bulk density of 0.50-0.60 g/cc and surface area of 10 m$^2$/g.

Example 2

Synthesis of Magnesium Alkoxide Particles without Stepwise Heating of Reactants Magnesium powder (5.5 kg) was added to mixture of alcohol having 65 Liters ethanol, 4 Liters Methanol and 2 liters isopropanol. 420 g of iodine was added in the form of solution in ethanol. Reaction mixture was heated to 50° C. and reaction was carried on till hydrogen evolution was stopped. The product was filtered and dried.

Example 3

Synthesis of Ziegler Natta Procatalyst Using Magnesium Alkoxide of Example 1

The magnesium alkoxide (50 kg) from example 1 was treated with a equal volume mixture of 1150 liters TiCl₄ and chlorobenzene in three step treatment at 100° C. Internal donor Ethyl Benzoate is added in first step. Benzoyl Chloride is added in the last step. After three stage treatment solid procatalyst is filtered and given four washes with 1000 liters isopentane each and then it is dried at 50° C. under stream of nitrogen. 55 kg of yellow colored procatalyst was obtained.

Example 4

Synthesis of Ziegler Natta Procatalyst Using Magnesium Alkoxide of Example 2

The magnesium alkoxide precursor (50 kg)) from example 2 was treated with a equal volume mixture of 1150 liters TiCl₄ and Chlorobenzene in a three stage treatment at 100° C. Internal donor ethyl benzoate is added in first step. Benzoyl Chloride is added in the last step. After three stage treatment solid procatalyst is filtered and given four washes with 1000 liters isopentane each then dried at 50° C. under stream of nitrogen. 53 kg of yellow colored procatalyst was obtained.

Example 5

Polymerisation of Propylene Using Procatalyst of Example 3

Solid procatalyst (0.08 g) of example 3 was mixed with triethyl alumunium cocatalyst (1.2 g) and paraethoxy ethylbenzoate (0.05 g). The catalysts were mixed in such proportions that the alumunium:titanium ratio is maintained at 250:1. The mole ratio of selectivity control agent to titanium was kept at 50:1. The catalyst was employed to polymerize propylene in slurry phase with hexane as the diluent under a constant propylene pressure of 5 kg for 1 hr at 70° C., followed by addition of 50 mmol of hydrogen to terminate the polymerization

Example 6

Polymerisation of Propylene Using Procatalyst of Example 4

Solid procatalyst (0.08 g) of example 4 was mixed with triethyl alumunium cocatalyst (1.2 g) and paraethoxy ethylbenzoate (0.05 g). The catalysts were mixed in such proportions that the alumunium:titanium ratio was maintained as 250:1. The mole ratio of selectivity control agent to titanium was kept at 50:1. The catalyst was employed to polymerize propylene in slurry phase with hexane as the diluent under a constant propylene pressure of 5 kg for 1 hr at 70° C., followed by addition of 50 mmol of hydrogen to terminate the polymerization.

TABLE 1

Comparative analysis of spheroidal magnesium alkoxide particles of example 1 and example 2

| Magnesium alkoxide prepared by | Methoxy content (wt %) | Ethoxy content (wt %) | i-propoxy content (wt %) | Mean Particle size (microns) | Span | Bulk Density (g/ml) | Crushing strength (kg) | circularity |
|---|---|---|---|---|---|---|---|---|
| Example 1 | 18.0 | 60.0 | nil | 34.0 | 0.82 | 0.59 | 30.2 | 0.72 |
| Example 2 | 7.0 | 70.0 | 1.5 | 26.0 | 0.95 | 0.48 | 16.8 | 0.65 |

TABLE 2

Comparative analysis of Zieglar Natta procatalyst synthesized by using the alkoxide particles of example 1 and example 2

| Procatalyst prepared by | Mean particle size | Span | Circularity |
|---|---|---|---|
| Example 3 | 34 | 1.14 | 0.73 |
| Example 4 | 13 | 2.87 | NA |

TABLE 3

Comparative analysis of polymer resins synthesized by using the ziegler natta procatalysts of example 3 and example 4

| Polymer resin prepared by | Mean particle size | Span | Bulk density | Circularity |
|---|---|---|---|---|
| Example 5 | 722 | 1.14 | 0.38 | 0.71 |
| Example 6 | 320 | 2.79 | 0.32 | NA |

Table 1 provides a comparative analysis of the magnesium alkoxide particles of the invention (prepared as in example 1) and of the alkoxide particles prepared as in example 2. The magnesium alkoxide particles of the invention had more circularity as compared to the magnesium alkoxide particles of example 2. Further, the crushing strength, particle size and bulk density of the particles of the invention are considerably higher than those prepared by example 2. The alkoxide particles of the invention possess narrow particle size distribution as evidenced by their low span values.

Table 2 compares the properties of the Ziegler natta procatalyst prepared (as in examples 3 and 4 respectively) by using the alkoxide particles of example 1 and example 2. It can be seen that there is shape replication during the procatalyst synthesis of example 3 and circularity as observed in the alkoxide particles is almost retained in the procatalyst. Further, particle size values of the procatalyst of the invention suggests negligible attrition for the particles of the invention. Further, the procatalyst prepared by the alkoxide particles of the invention has narrow particle size distribution as evidenced by their low values of span.

Table 3 compares the properties of the polymer resin prepared (as in examples 5 and 6) by using the procatalyst of example 5 and example 6. The resin particles prepared by example 5 have high particle size, narrow particle size distribution as well as high bulk density and circularity as compared to the resin particles prepared by example 6.

Figure 2:
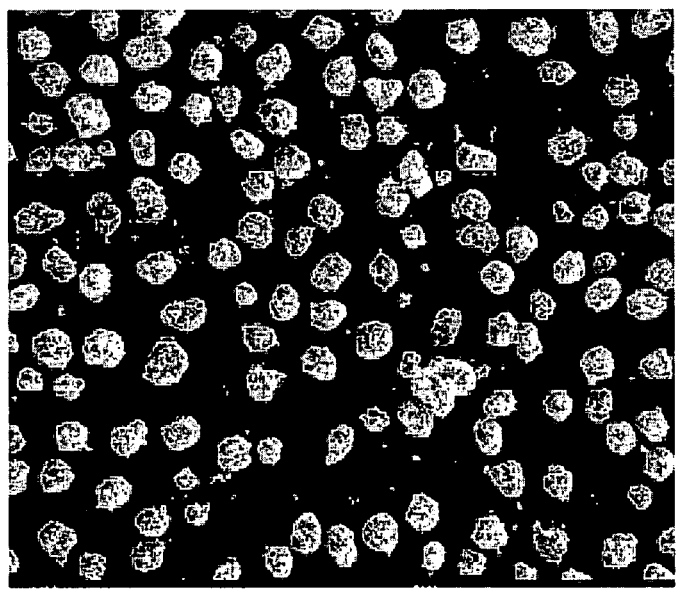
Figure 3:
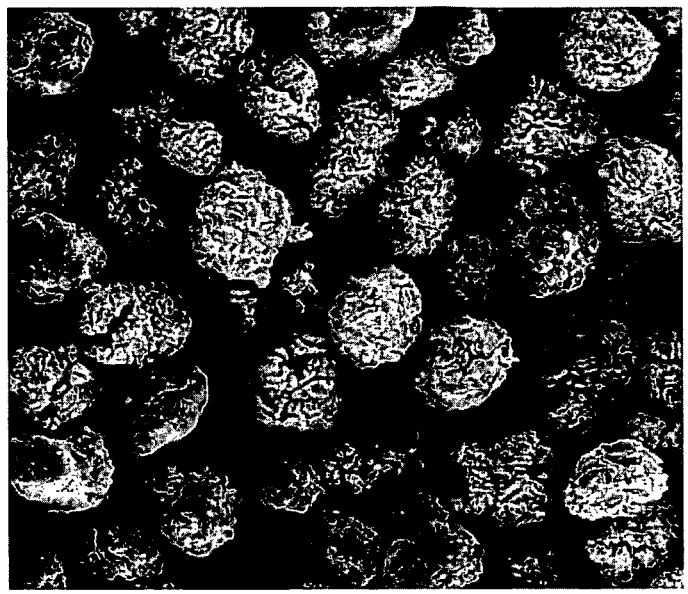
Figure 4:
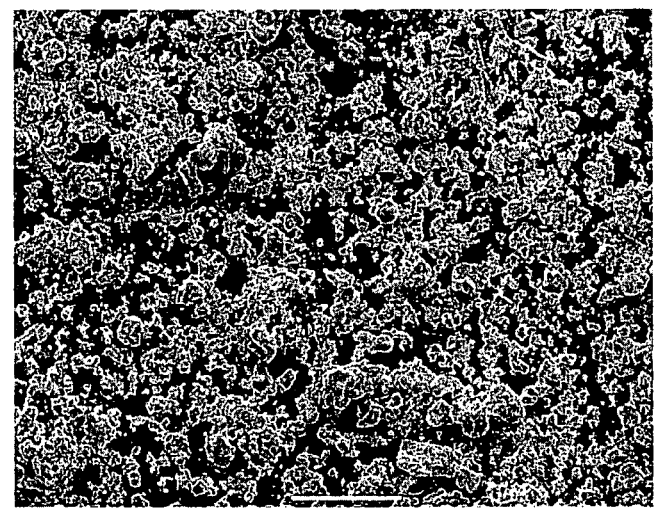
Figure 5:
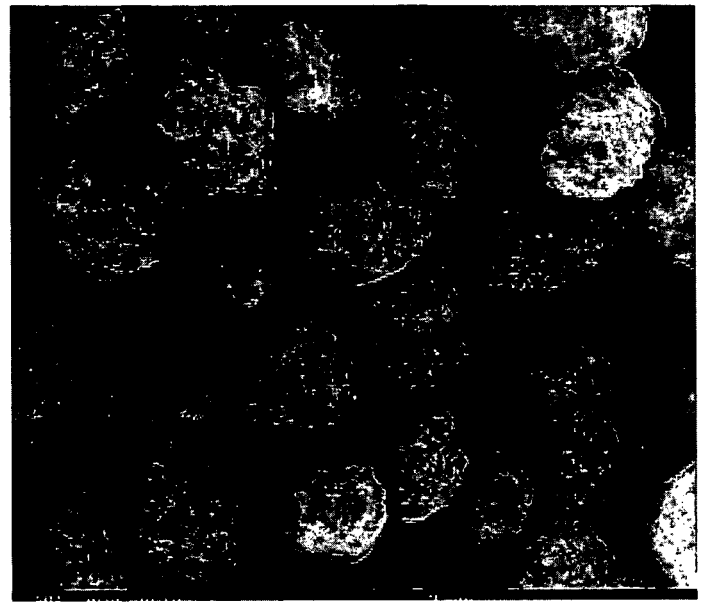
Figure 6:
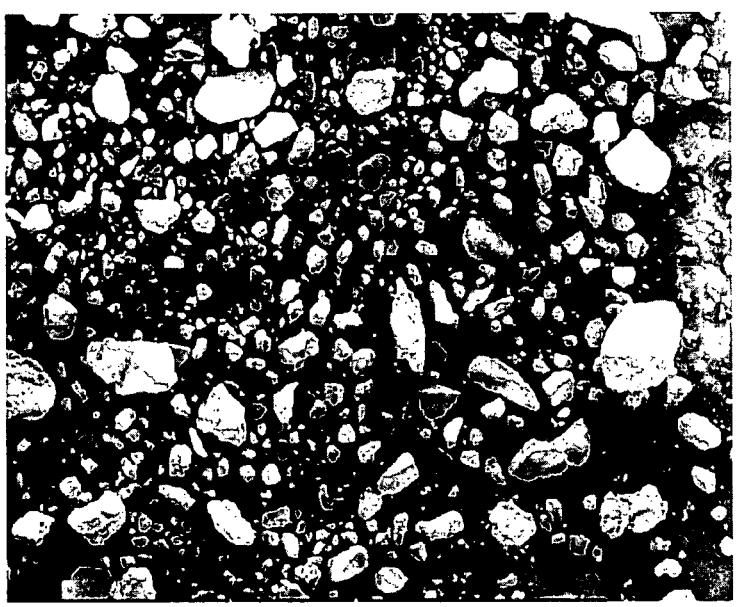

The morphology of the alkoxide particles, procatalyst particles and the resin particles of the invention is compared in the respective SEM images of the particles. FIG. 1, FIG. 3 and FIG. 5 of the accompanying drawings present the SEM images of the alkoxide particles, of the procatalyst particles and of the resin particles of the invention. FIG. 2, FIG. 4 and FIG. 6 of the accompanying drawings present the SEM images of the alkoxide particles, of the procatalyst particles and of the resin particles prepared by example 2, example 4 and example 6 respectively. It can be clearly observed that the particles of the invention have regular spheroidal morphology which is retained during the procatalyst synthesis as well as during the resin synthesis.

The invention, thus provides crystalline magnesium alkoxide particles having improved mechanical strength and narrow particle size distribution. Further, the alkoxide particles of the invention retains its morphology and particle size during subsequent procatalyst synthesis on a large scale. Furthermore, the retention of particle morphology is observed during the synthesis of the polymer resin. Therefore the magnesium alkoxide particles of the invention are suitable as precursors for the synthesis of regular shaped procatalyst and polymer resin. The invention also provides an economical, safe and environmentally friendly method for the synthesis of magnesium alkoxide particles by providing means for recovery and reuse of alcohol vapours during the alkoxide synthesis as well as by providing means for venting off the hydrogen gas produced during the synthesis.

The above description is illustrative only and is not limiting. The present invention is defined by the claims that follow and their full range of equivalents.

The invention claimed is:

1. A process for the synthesis of spheroidal magnesium alkoxide, the process comprising reacting magnesium metal, in the presence of iodine, with a mixture of at least two alcohols by heating the mixture of magnesium metal, iodine, and the at least two alcohols first in the range of 40° C. to 65° C. for a period of 2 hours and then in the range of 65° C. to 80° C. for a period of 1 hour, maintaining the reaction at 80° C. for a period of 6 to 10 hours, and recovering and recycling the alcohols to the reaction.

2. The process as claimed in claim 1, wherein the mixture of alcohols is selected from the group consisting of methanol, ethanol, propanol, isopropanol, butanol and isobutanol.

3. The process as claimed in claim 1, wherein the mole ratio of magnesium to the mixture of alcohols is in the range of 1:2 to 1:20.

4. Spheroidal magnesium alkoxide particles produced according to the process of claim 1, wherein the particles have a circularity in the range of 0.5 to 1.0, a mean particle size in the range of 25 microns to 65 microns, a bulk density in the range of 0.45 g/cc to 0.65 g/cc, a surface area in the range of 1 to 20 m$^2$/g, a crushing strength of at least 20 kg, a span of up to 0.82 and exhibit a diffraction pattern comprising peaks at 2θ values of about 9.8, 10.2, 10.4 and 11.9 on irradiation with a Cu Kα radiation having a wavelength of 1.5406 Å.

5. A method for synthesis of a Ziegler-Natta procatalyst comprising an internal electron donor, the method comprising reacting the spheroidal magnesium alkoxide obtained by the process of claim 1, with TiCl$_4$ and chlorobenzene, to obtain a product comprising TiCl$_4$, MgCl$_2$ and a reaction side product having the formula TiCl$_x$(OR$^1$)$_y$(OR$^2$)$_z$, where x, y, and z are integers of from 0 to 4, and each of R$^1$ and R$^2$ is an alkyl or an aryl group, and then treating the reaction side product with a carboxylic acid chloride to generates in situ internal donor(s) for the procatalyst.

6. The method as claimed in claim 5, wherein the procatalyst has a particle size in the range of 25 to 65 microns.

7. The method as claimed in claim 5, wherein the internal donor(s) is/are methyl benzoate, ethyl benzoate, n-propyl benzoate, i-propyl benzoate, n-butyl benzoate, i-butyl benzoate, dimethyl phthalate, diethyl phthalate, dipropyl phthalate, di-isopropyl phthalate, di-butyl phthalate or di-isobutyl phthalate.

* * * * *